(12) United States Patent
Sillman

(10) Patent No.: US 7,125,523 B2
(45) Date of Patent: Oct. 24, 2006

(54) HOLDERS FOR ARRAYS

(75) Inventor: Debra A. Sillman, Los Altos, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 660 days.

(21) Appl. No.: 10/135,901

(22) Filed: Apr. 29, 2002

(65) Prior Publication Data

US 2003/0203492 A1   Oct. 30, 2003

(51) Int. Cl.
*B01L 9/00* (2006.01)

(52) U.S. Cl. .......................... 422/104; 422/63; 422/67; 422/99; 422/102

(58) Field of Classification Search ................. 422/55, 422/63, 65, 67, 99, 102, 104
See application file for complete search history.

(56) References Cited

U.S. PATENT DOCUMENTS

| | | | |
|---|---|---|---|
| 4,159,875 A | | 7/1979 | Hauser |
| 4,501,495 A | * | 2/1985 | Faulkner et al. ............ 356/244 |
| 5,592,289 A | | 1/1997 | Norris |
| 5,869,006 A | * | 2/1999 | Fanning et al. ............... 422/67 |
| 5,919,553 A | * | 7/1999 | Kavanaugh ............... 428/195.1 |
| 6,132,685 A | * | 10/2000 | Kercso et al. ............... 422/104 |
| 6,171,780 B1 | * | 1/2001 | Pham et al. ..................... 435/4 |
| 6,180,351 B1 | | 1/2001 | Cattell |
| 6,215,894 B1 | | 4/2001 | Zeleny et al. |
| 6,258,326 B1 | * | 7/2001 | Modlin ....................... 422/102 |
| 6,372,428 B1 | | 4/2002 | Nova et al. |
| 6,406,849 B1 | | 6/2002 | Dorsel et al. |
| 6,556,923 B1 | * | 4/2003 | Gallagher et al. ............. 702/23 |
| 6,699,437 B1 | * | 3/2004 | Astle .......................... 422/102 |
| 6,827,901 B1 | * | 12/2004 | Copeland et al. ............. 422/64 |
| 6,864,097 B1 | * | 3/2005 | Schembri et al. ........... 436/165 |

FOREIGN PATENT DOCUMENTS

WO  WO 00/23803  4/2000

* cited by examiner

*Primary Examiner*—Jill Warden
*Assistant Examiner*—Dwayne K Handy

(57) ABSTRACT

A holder for an array unit having a planar substrate and an array of chemical moieties on a surface of the substrate. The holder may include a body with a retaining mechanism which releasably retains an array unit in a seated position. A holder identifier may include data on a characteristic of the holder or seated array or be linkable to a file containing such information. An apparatus, method, and computer program product which may be used with such a holder are also provided.

16 Claims, 10 Drawing Sheets

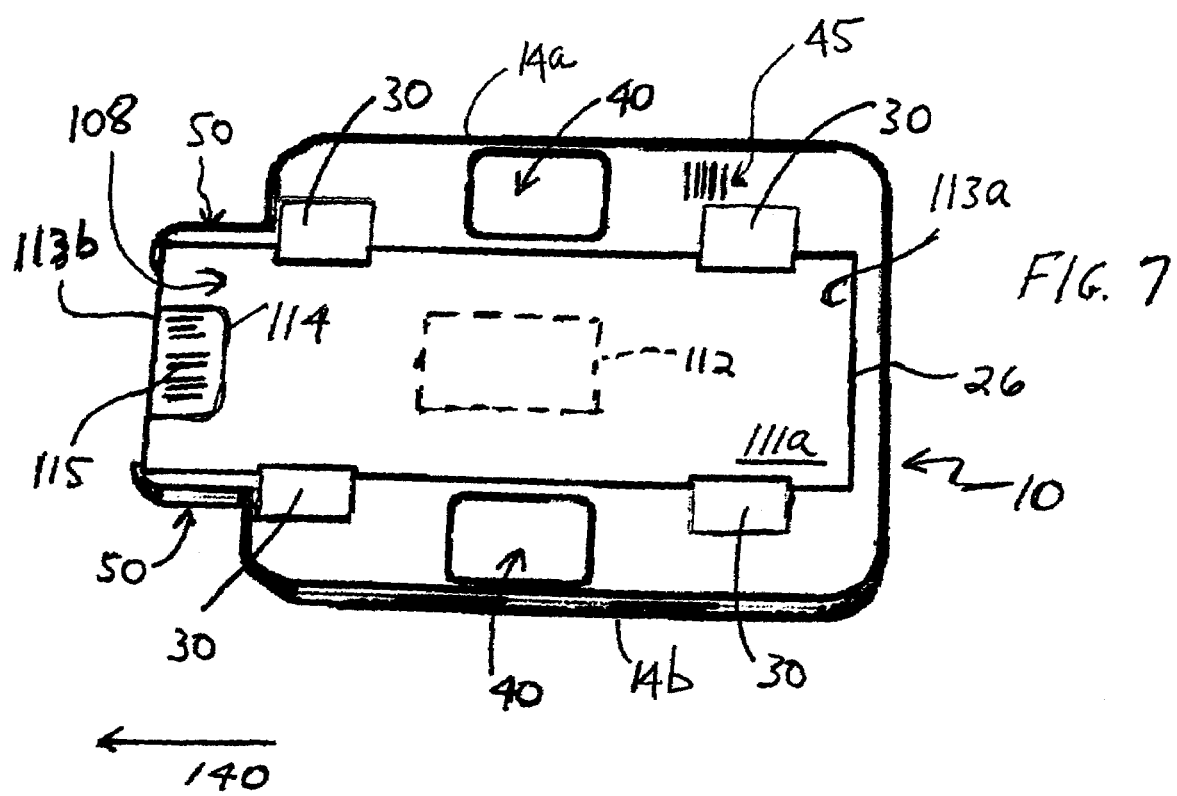

HOLDERS FOR ARRAYS

FIELD OF THE INVENTION

This invention relates to holders for arrays, particularly biopolymer arrays such as DNA or protein arrays, which are useful in diagnostic, screening, gene expression analysis, and other applications.

BACKGROUND OF THE INVENTION

Polynucleotide arrays (such as DNA or RNA arrays) and peptide array, are known and may be used, for example, as diagnostic or screening tools. Such arrays include regions (sometimes referenced as spots or features) of usually different sequence polynucleotides or peptides arranged in a predetermined configuration on a substrate. The array is "addressable" in that different features have different predetermined locations ("addresses") on a substrate carrying the array.

Biopolymer arrays can be fabricated using in situ synthesis methods or deposition of the previously obtained biopolymers. The in situ fabrication methods include those described in U.S. Pat. No. 5,449,754 for synthesizing peptide arrays, and in U.S. Pat. No. 6,180,351 and WO 98/41531 and the references cited therein for polynucleotides. In situ methods also include photolithographic techniques such as described, for example, in WO 91/07087, WO 92/10587, WO 92/10588, and U.S. Pat. No. 5,143,854. The deposition methods basically involve depositing biopolymers at predetermined locations on a substrate which are suitably activated such that the biopolymers can link thereto. Biopolymers of different sequence may be deposited at different feature locations on the substrate to yield the completed array. Procedures known in the art for deposition of biopolymers, particularly DNA such as whole oligomers or cDNA, are described, for example, in U.S. Pat. No. 5,807,522 (touching drop dispensers to a substrate), and in PCT publications WO 95/25116 and WO 98/41531, and elsewhere (use of a pulse jet in the form of a piezoelectric inkjet head).

Further details of large scale fabrication of biopolymer arrays by depositing either previously obtained biopolymers or by the in situ method, are disclosed in U.S. Pat. Nos. 6,242,266, 6,232,072, 6,180,351, and 6,171,797.

In array fabrication, the quantities of DNA available for the array are usually very small and expensive. Sample quantities available for testing are usually also very small and it is therefore desirable to simultaneously test the same sample against a large number of different probes on an array. These conditions require the manufacture and use of arrays with large numbers of very small, closely spaced features.

The arrays, when exposed to a sample, will exhibit a binding pattern. The array can be read by observing this binding pattern by, for example, labeling all targets such as polynucleotide targets (for example, DNA), in the sample with a suitable label (such as a fluorescent compound), scanning an illuminating beam across the array and accurately detecting the fluorescent signal from the different features of the array. Assuming that the different sequence polynucleotides were correctly deposited in accordance with the predetermined configuration, then the observed binding pattern will be indicative of the presence and/or concentration of one or more polynucleotide components in the sample. Peptide or arrays of other chemical moieties can be used in a similar manner. Techniques and apparatus for scanning chemical arrays have been described, for example, in U.S. Pat. Nos. 5,763,870 and 5,945,679. Apparatus which reads an array by scanning an illuminating beam by the foregoing technique are often referred to as scanners and the technique itself often referred to as scanning. Conventionally, such scanning has been done by illuminating array features on a front surface of the substrate one pixel at a time. Array scanners typically use a laser beam as a light source, which is scanned over pixels covering the array features. A detector (typically a fluorescence detector) with a very high light sensitivity is normally desirable to achieve maximum signal-to-noise in detecting hybridized molecules, particularly in array scanners used for DNA sequencing or gene expression studies. At present, photomultiplier tubes ("PMTs") are still the detector of choice although charge coupled devices ("CCDs") and avalanche photodiodes ("APDs") can also be used. PMTs and APDs are typically used for temporally sequential scanning of array features, while CCDs permit scanning many features in parallel (for example, one line of features simultaneously, in which case an illuminating line may be used).

Polynucleotide arrays have previously been provided in two formats (sometimes referenced as "array units"). In one format, the array is provided as part of a package in which the array itself is disposed on a first side of a glass or other transparent substrate. This substrate is fixed (such as by adhesive) to a housing with the array facing the interior of a chamber formed between the substrate and housing. An inlet and outlet may be provided to introduce and remove sample and wash liquids to and from the chamber during use of the array. The entire package may then be inserted into a laser scanner, and the sample exposed array may be read through a second side of the substrate.

In another format, the array is present on an unmounted glass or other transparent slide substrate. This array is then exposed to a sample optionally using a temporary housing to form a chamber with the array substrate. The slide may then be placed in a laser scanner to read the exposed array. Most slide scanners require that the user manually insert the slide into a holder within the scanner. Some scanners allow the slide to rest on a surface while others clamp it to a known location using various types of guides. However, this exposes the fragile slide to the risk of chipping or breaking with consequent loss of what may be a very expensive array which itself may carry the results of an expensive and difficult to reproduce experiment. Perhaps even worse, minor damage such as smudges or scratches may go unnoticed to a user but can cause highly erroneous results to be read from the very small features of the array.

One of the problems recognized by the present invention, of using array holders, is as follows. First, different manufacturers may wish to construct array holders of different configurations (for example, to include a hybridization chamber). This can lead to a problem in that different array holders may position the array substrate, and hence the array, at different spatial locations within the scanner depending on the particular dimensions of the array holder. To avoid wasted time and misleading data, the scanner is set to scan only the area of the array on the slide. To do this the scanner needs to know where the array is physically located inside the scanner. Knowing where the array is located inside the scanner also avoids misinterpretation of read data as a result of incorrectly assuming that a location in a scanned image (for example, a corner feature) is the actual location on the array (for example, the corner). While this may not be a problem if all users were to use a standard size slide for all arrays (such as the well accepted 1"×3' microscope slide), the introduction of various non-standardized holders causes the array location within the scanner to vary. Another problem recognized by the present invention is that some scanners may not actually be able to physically accommodate some holders and could be damaged by their attempted loading into the scanner. Further, to keep array manufacturing costs low, it may be desirable to use non-standard substrate sizes in which case it becomes useful for the scanner to know in advance both the location and the size of the substrate containing the array. This can be particularly important where it is possible to damage the reader or holder should reader attempt to read an area (such as by laser illumination of it) where no substrate is present.

The present invention recognizes that it would be desirable then to have some means for an array reader to obtain information on one or more characteristics of an array holder or an array unit.

SUMMARY OF THE INVENTION

The present invention then, provides in one aspect, a holder for an array unit having a planar substrate and an array of chemical moieties on a surface of the substrate (and can optionally include the array unit itself). The holder may include a body with a retaining mechanism which releasably retains an array unit in a seated position, such that an array unit can be repeatedly inserted into and removed from the seated position in which it is retained in the holder. The holder also includes a machine readable holder identifier. Such an identifier may include data on a characteristic of the holder or seated array, or may be linkable to a file (for example in a memory device) carrying such data. Such data on a characteristic may include data on a spatial characteristic, such as a position or dimension of the holder or an array unit seated in the holder, and more particularly data on a position or dimension of the substrate or array within the array unit (for example, location and size either).

The present invention also provides a method of reading an array of chemical moieties on a substrate of an array unit. The method may include seating the array unit in a holder, which holder carries a holder identifier, and may further include mounting the holder with seated array into an array reader. The holder identifier is read and a characteristic of the holder is retrieved based on the read holder identifier. As mentioned above, such retrieval may be directly from the read identifier or from a file linked to the identifier (for example, having a file name the same as that carried by the identifier). The array may also be read. The method may also include any of the procedures executed by an apparatus of the present invention. In another method of the present invention the holder identifier may be read (with or without a seated array), a characteristic of the holder retrieved based on the read identifier, and when the retrieved characteristic does not meet a predetermined condition (for example, suitability for use in a particular reader or a tolerance for one or more holder dimensions), the holder or a seated array for reading is rejected or an operator alert generated.

In another aspect of the present invention there is provided an apparatus for reading an array of chemical moieties on a substrate of an array unit. This apparatus may include a receptacle into which is mountable a holder carrying a seated array unit, which holder carries a holder identifier, as well as a reader system and a processor. The reader system reads the holder identifier and data from different chemical moieties of the array, and the processor retrieves data on a characteristic of the holder or array unit based on the read holder identifier, and may cause the apparatus to execute any other feature of a method of the present invention. The reader system may be one reader which reads both the array and any or both of the identifiers herein, or may include a first identifier reader to read the holder identifier (and optionally also read the array unit identifier or a second identifier reader may be provided for this purpose), and an array reader to read the data from the different chemical moieties of the array. The processor may also do any one or more of the following: compare the retrieved data on a characteristic of the holder with a predetermined condition in a memory and, when the retrieved characteristic does not meet the predetermined condition, generate a user alert or inhibit reading of data from different chemical moieties of the array; control a position or dimension of an area over which the interrogating light is scanned based on data retrieved using the read holder identifier and optionally also based on data retrieved using the read array unit identifier.

A computer program product is also provided by the present invention. The computer program may be used with an apparatus of the present invention and may execute a method of the present invention. The program product has a computer program stored thereon for reading the holder identifier and retrieving data on a characteristic of the seated array unit (such as its position or a dimension) based on the read holder identifier. The computer program may also cause the processor to perform any of its functions in an apparatus of the present invention.

In any aspect of the present invention a holder characteristic can include, for example, data on a holder or array unit dimension or position (such as the position of the seated array unit) or an indication of the suitability of the holder in particular types of readers. In the case of position or dimension data this may include data on any one or more of the following for the holder or seated array unit (including any feature on either): x position or dimension; y position or dimension; z position or dimension; angular orientation. Note that x and y are the directions along the length and width of the substrate and z is the direction perpendicular to the substrate. Also, the seated array unit may additionally include a machine readable array unit identifier which may either contain information on a characteristic of the array unit (such as an array layout, position of the array on a substrate, or one or more dimensions of the array) or be linkable to a file containing such information. Examples of any of the identifiers mentioned herein include bar codes or data carried in a memory (such as an optical, magnetic, or solid state memory) attached to the holder (for the holder identifier) or array substrate or housing (for the array identifier). The reading of the array may be accomplished by various methods, such as scanning an interrogating light over the array (for example, a light spot scanned across the array in an x and y direction where x and y are the directions along a length and width of the array). For this purpose an apparatus of the present invention may also be provided with a reading system which may also read one or more of the holder and array unit identifiers.

Different embodiments of methods and devices of the present invention can provide any or more of a number of useful features. For example, information on a characteristic of a holder or array unit can be provided to the array reader which information can be used, for example, to control the reading of the array or generate a user alert when appropriate.

BRIEF DESCRIPTION OF THE DRAWINGS

Embodiments of the invention will now be described with reference to the drawings, in which:

FIG. 7 is the same as FIG. 6 but showing the slide in the mounted position on the holder;

To facilitate understanding, the same reference numerals have been used, where practical, to designate elements that are common to the figures.

DETAILED DESCRIPTION OF EMBODIMENTS OF THE INVENTION

Figure 1:
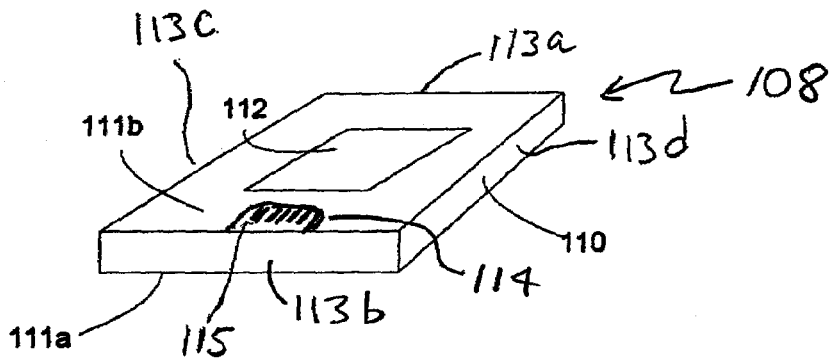
FIG. 1 illustrates a slide carrying an array, of the present invention, and such as may be used in a holder and methods of the present invention.

In the present application, unless a contrary intention appears, the following terms refer to the indicated characteristics. A "biopolymer" is a polymer of one or more types of repeating units. Biopolymers are typically found in biological systems and particularly include polysaccharides (such as carbohydrates), and peptides (which term is used to include polypeptides and proteins) and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. For example, a "biopolymer" includes DNA (including cDNA), RNA, oligonucleotides, and PNA and other polynucleotides as described in U.S. Pat. No. 5,948,902 and references cited therein (all of which are incorporated herein by reference), regardless of the source. An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (for example, a single amino acid or nucleotide with two linking groups one or both of which may have removable protecting groups). A biomonomer fluid or biopolymer fluid reference a liquid containing either a biomonomer or biopolymer, respectively (typically in solution).

An "array", unless a contrary intention appears, includes any one-, two- or three-dimensional arrangement of addressable regions bearing a particular chemical moiety or moieties (for example, biopolymers such as polynucleotide sequences) associated with those regions. An array is "addressable" in that it has multiple regions with a different moiety or moieties (for example, different polynucleotide sequences) on each region such that a region (also referenced as a "feature" or "spot" of the array) at a particular predetermined location (an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various features. However, either of the "target" or "target probes" may be the one which is to be evaluated by the other (thus, either one could be an unknown mixture of polynucleotides to be evaluated by binding with the other). An "array layout" refers to one or more characteristics of the features, such as feature positioning on the substrate, one or more feature dimensions, and an indication of a moiety at a given location. "Hybridizing" and "binding", with respect to polynucleotides, are used interchangeably.

When one item is indicated as being "remote" from another, this is referenced that the two items are at least in different buildings, and may be at least one mile, ten miles, or at least one hundred miles apart. "Communicating" information references transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. Wavelengths are peak wavelengths unless otherwise indicated. By "transparent" is referenced a substrate which transmits, within the substance, at least 80% (or even at least 85%, 90%, 95%, or 98%) of both the interrogating and emitted light as measured at the peak wavelengths. These transmission figures represent transmission within the bulk substance and exclude any account of Fresnel reflection that may occur upon light entering the substance at an interface of that substance and another medium (for example, the interface of a surface of the substance and the ambient atmosphere). By "reflective" material is a material which reflects at least 60% (or even at least 80% or 90%) of light of the interrogating or emitted wavelength as a result of the nature or construction of the material and not as a result of Fresnel reflection. Such reflective materials may include a metal or semiconductor (for example, silicon) layer.

Words such as "front", "rear", "back", "leading", "trailing", "top", "upper", and "lower", as used in this application are all used in a relative sense only. "Fluid" is used herein to reference a liquid. Furthermore, when one thing is "slid" or "moved" or the like, with respect to another, this implies relative motion only such that either thing or both might actually be moved in relation to the other.

A "spatial characteristic" of an object (for example the holder or array unit) is used herein to describe any characteristic of the object or some part of it in space, including position or relative or absolute dimension or orientation. A "spatial characteristic" therefore includes a "position" or "dimension" as well as angular orientation. The "position" of an object includes any information on the location of the object (or some part of it) in space (for example, location along one or more axes or angular orientation ) while a "dimension" of an object includes any one or more of length, width, or thickness of the object or some part of it such as an array unit substrate or array). Other spatial characteristics can, for example, include qualitative measures (for example, "this holder is too big for most readers").

A "processor" references any hardware and/or software combination which will perform the functions required of it. For example, any processor herein may be a programmable digital microprocessor such as available in the form of a mainframe, server, or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic or optical disk may carry the programming, and can be read by a suitable disk reader communicating with each processor at its corresponding station. Reference to a singular item, includes the possibility that there are plural of the same items present. "May" means optionally. Methods recited herein may be carried out in any order of the recited events which is logically possible, as well as the recited order of events. All patents and other references cited in this application, are incorporated into this application by reference except insofar as they may conflict with the present application (in which case the present application prevails).

Figure 2:
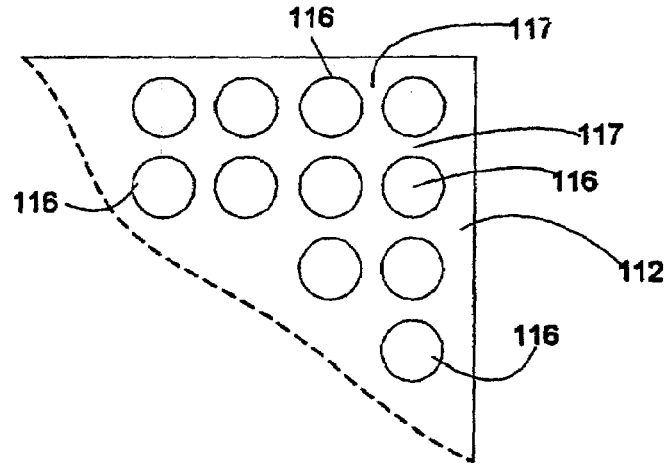
FIG. 2 is an enlarged view of a portion of FIG. 1 showing ideal spots or features.
Figure 3:
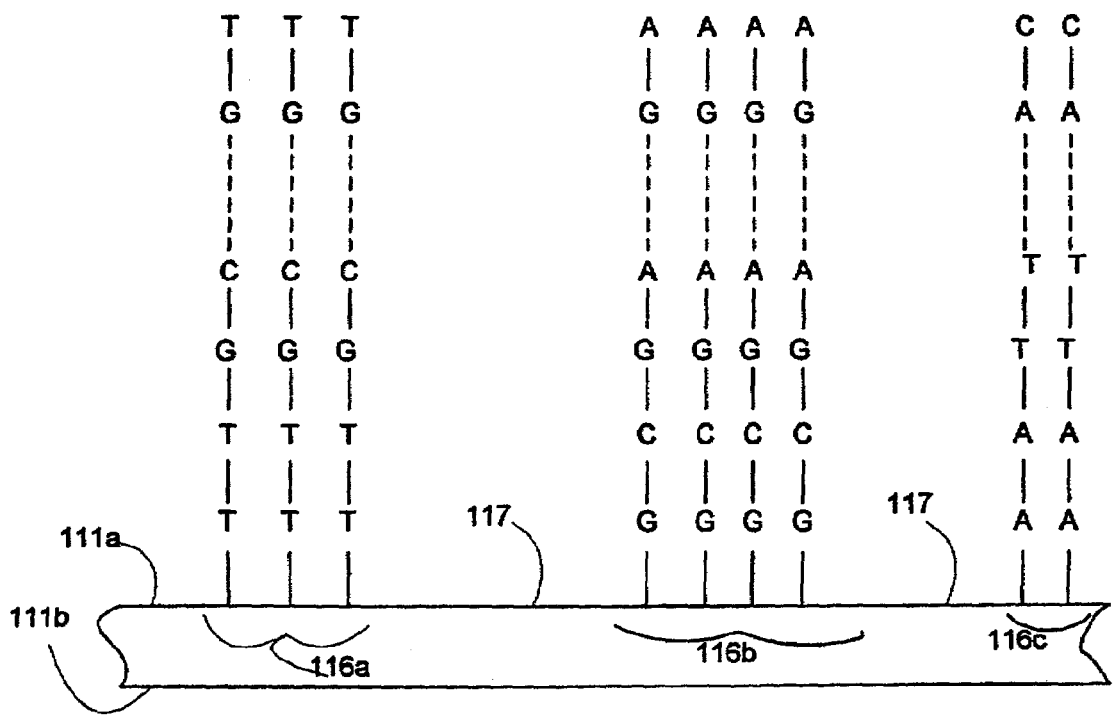
FIG. 3 is an enlarged illustration of a portion of the substrate in FIG. 2.
Figure 4:
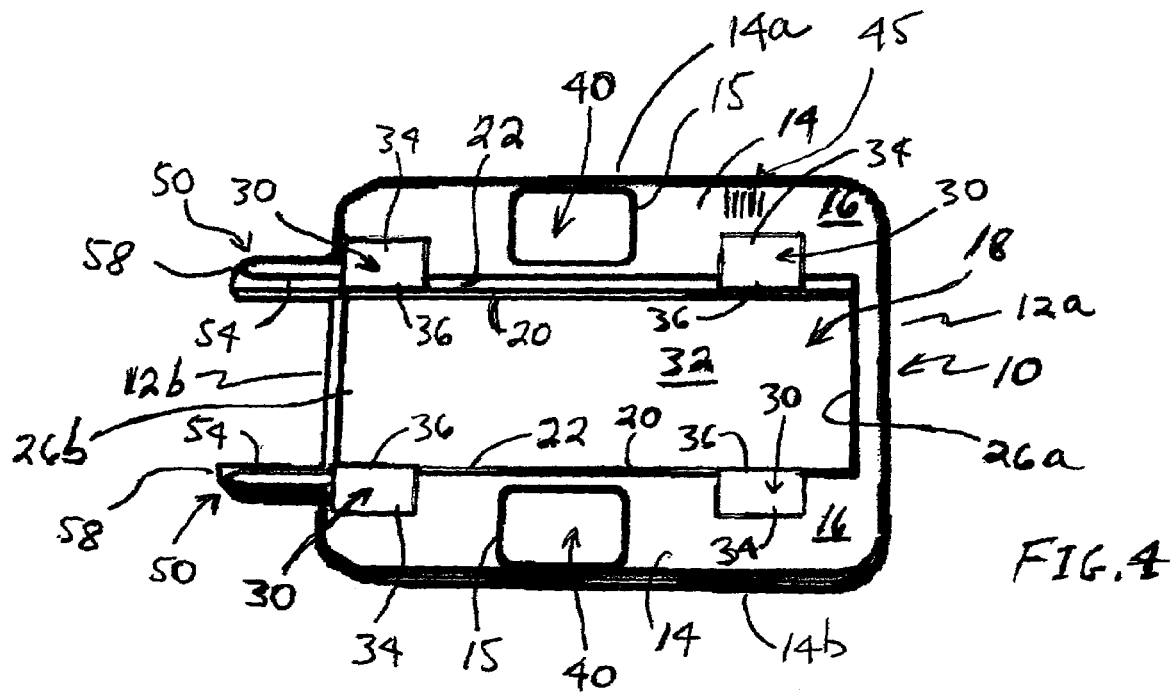
FIG. 4 is a front view of a holder of the present invention.
Figure 6:
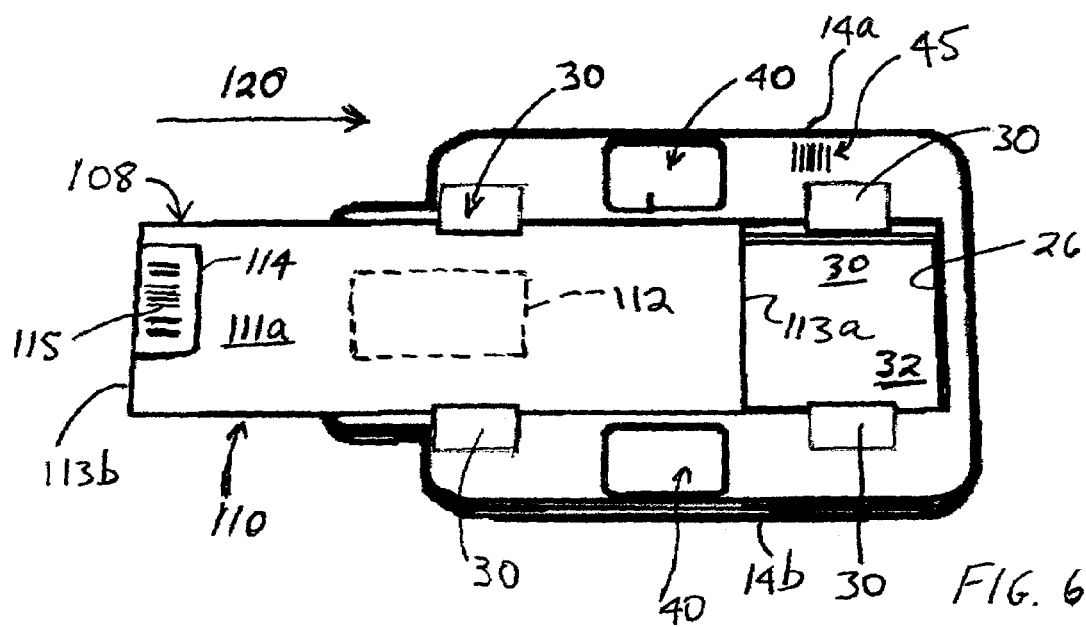
FIG. 6 is a view the same as that of FIG. 4 but showing a slide of FIG. 1 being slid into the mounted position on the holder.
Figure 5:
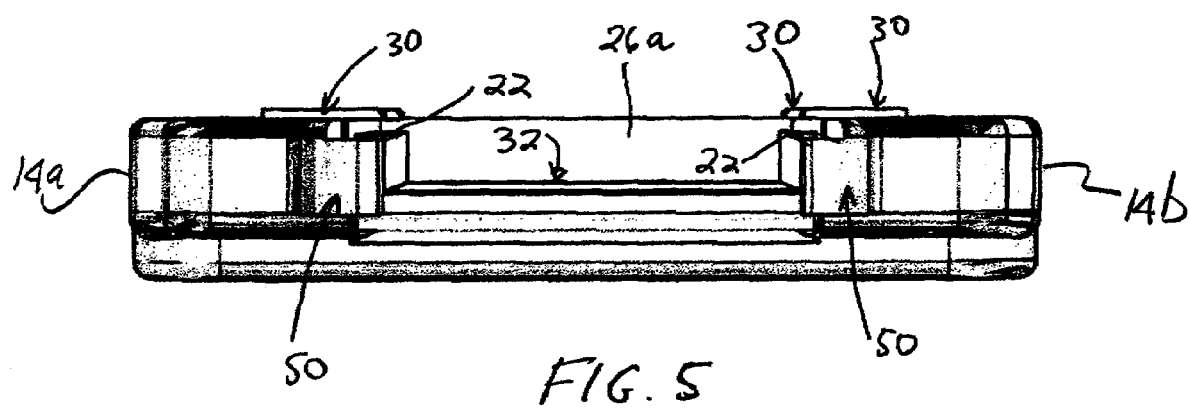
FIG. 5 is a leading end elevation of the holder of FIG. 1.

Referring first to FIGS. 1–3, typically methods and apparatus of the present invention uses an array unit 108, which includes a contiguous planar transparent substrate in the form of slide 110 carrying an array 112 disposed on a rear surface 111$b$ of substrate 110. It will be appreciated though, that more than one array (any of which are the same or different) may be present on rear surface 111$b$, with or without spacing between such arrays. Note that one or more arrays 112 together will only cover a portion of the rear surface 111$b$, with regions of the rear surface 111$b$ adjacent the opposed sides 113$c$, 113$d$ and leading end 113$a$ and trailing end 113$b$ of slide 110, not being covered by any array 112. A front surface 111$a$ of the slide 110 does not carry any arrays 112. However, array 112 may optionally be on the front surface 111$a$ with rear surface 111$b$ not carrying any arrays 112. Each array 112 can be designed for testing against any type of sample, whether a trial sample, reference sample, a combination of them, or a known mixture of polynucleotides (in which latter case the arrays may be composed of features carrying unknown sequences to be evaluated). Slide 110 may be of any shape, and any holder used with it adapted accordingly, although slide 110 will typically be rectangular in practice. Array 112 contains multiple regions 116 (sometimes referenced as "spots" or "features") of biopolymers in the form of polynucleotides (in FIG. 3, A, C, G, T represent the usual nucleotides).

The array 12 may cover an area of less than 100 cm$^2$, or even less than 50, 10 or 1 cm$^2$. A typical array may contain at least ten features 116, or at least 100 features, at least 1,000, at least 100,000 features, or more. All of the features 116 may be of different composition, or some could be the same (for example, when any repeats of each feature composition are excluded the remaining features may account for at least 5%, 10%, 20%, 50% or 60% of the total number of features). Each feature 116 carries probes in the form of a one moiety or mixture of moieties, which in the case of each feature 116 in FIGS. 1–3 is a polynucleotide having a particular sequence, while interfeature areas 117 do not carry any moieties of a type the same as the features 116 (for example, no polynucleotides in the case of features 116 carrying polynucleotides). This is illustrated schematically in FIG. 3 where regions 116$a$, 116$b$, 116$c$ are shown as carrying different polynucleotide sequences. Features 116 may have widths (that is, diameter, for a round spot) of at least 5 or 10 μm, and less than 1.0 cm. In embodiments where very small spot sizes or feature sizes are desired, each of the features 116 may have widths of at least 1.0 μm and less than 1.0 mm, usually less than 500 μm, and more usually less than 200 μm. Features which are not round may have areas equivalent to the area ranges of round features 116 resulting from the foregoing diameter ranges. The probes of features 116 are typically linked to substrate 110 through a suitable linker, not shown.

Suitable materials for substrate 110 include any rigid material which may be non-porous to aqueous solutions, for example, silica, glass, or a plastic (that is, a synthetic or processed high molecular weight polymer that is, or is not, thermosetting or thermoplastic). Rear surface 111$b$ should ideally exhibit a low level of binding during hybridization or other events. In many embodiments, the slide will be shaped generally as a rectangular solid, having a length in the range about 5 mm to 100 cm, usually about 10 mm to 25 cm, more usually about 10 mm to 15 cm; a width in the range about 4 mm to 25 cm, usually about 4 mm to 10 cm and more usually about 5 mm to 5 cm; and a thickness in the range about 0.01 mm to 5.0 mm, usually from about 0.1 mm to 2 mm and more usually from about 0.2 to 1 mm.

An array identifier 115 in the form of a machine readable bar code, is associated with the array 112, by being provided on the same substrate 110 adjacent one of the arrays 112. For example, identifier 115 could be printed on a label 114 adhesively attached to substrate 110 or printed directly onto substrate 110. Of course, codes other than a bar code could be used (for example, a solid state, magnetic or optical memory carrying the identifier 40 could be provided). In the case where more than one array 112 is present on the same substrate 110, a separate identifier can be provided adjacent each corresponding array 112 if desired. Identifier 115 may contain information on a characteristic of array unit 108, such as information on the layout of array 112 as well as information on the x and y positions or dimensions of array 112 on substrate 110 or z position information of array 112 (where x and y are the directions along the length and width of the substrate and hence also along the length and width of array 112, and z is the direction perpendicular to the substrate plane defined by x and y). Alternatively, identifier may be linkable to a file containing the foregoing information in a manner such as described in U.S. Pat. No. 6,180,351. Each identifier 115 for different arrays 112 may be unique so that a given identifier will likely only correspond to one array 112 or to arrays 112 on the same substrate 110. This can be accomplished by making identifier 115 sufficiently long and incrementing or otherwise varying it for different arrays 112 or arrays 112 on the same substrate 110, or even by selecting it to be globally unique in a manner in which globally unique identifiers are selected as described in U.S. Pat. No. 6,180, 351.

Arrays such as those of FIGS. 1–3 can be fabricated using drop deposition from pulse jets of either polynucleotide precursor units (such as monomers) in the case of in situ fabrication, or the previously obtained polynucleotide. Such methods are described in detail in, for example, the previously cited references including U.S. Pat. Nos. 6,242,266, 6,232,072, 6,180,351, 6,171,797, 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, other array fabrication methods may be used such as described in U.S. Pat. Nos. 5,599,695, 5,753,788, and 6,329,143. Interfeature areas 117 need not be present particularly when the arrays are made by light directed methods as described in those patents.

For the purposes of the discussions below, it will be assumed (unless the contrary is indicated) that the array 112 is a polynucleotide array formed by the deposition of previously obtained polynucleotides using pulse jet deposition units. However, it will be appreciated that an array of other polymers or chemical moieties generally, whether formed by multiple cycle in situ methods adding one or more monomers per cycle, or deposition of previously obtained moieties, or by other methods, may be present instead.

Figure 9:
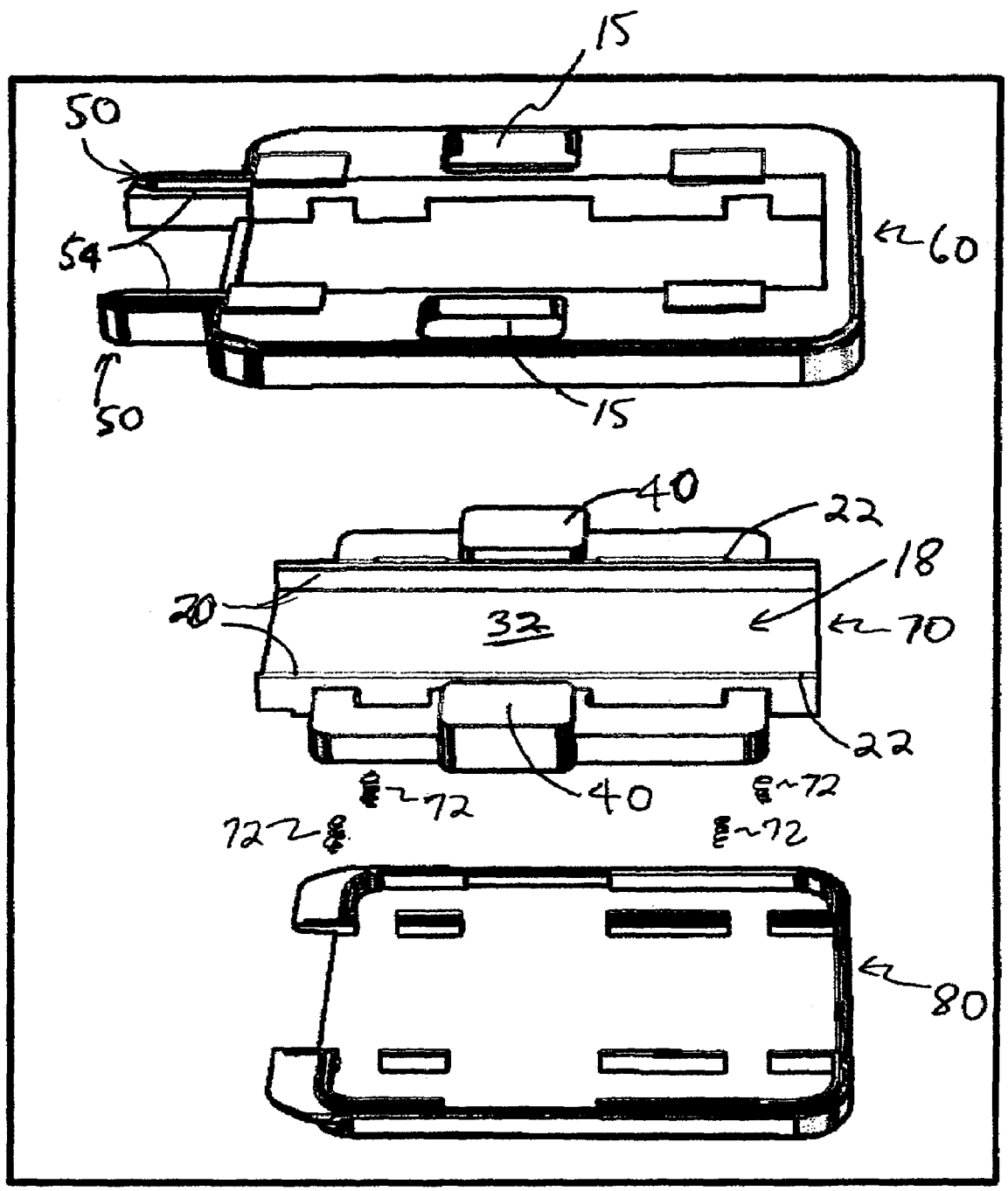
FIG. 9 is an exploded view of the holder of FIG. 1.

Turning now to FIG. 4–7, a holder 10 of the present invention will now be described in more detail. Holder 10 has a body which is generally rectangular in shape and includes two opposed side portions 14 with a channel 18 positioned therebetween, and extending in a direction between ends 12a, 12b of the body. Side portions 14 have respective side edges 14a. Channel 18 has a bottom surface 32 which acts as a backer member, and has a closed leading end 26a and an open trailing end 26b. Opposed sides 20 of channel 18 have ledges 22 running the length of the sides 20. Portions of ledges 22 act as a movable set of rear clamp members, as will shortly be described. Four tabs 30 positioned about channel 18, have outside portions 34 attached to side portions 14 and inside portions 36 which extend over ledges 22 and are slightly spaced therefrom in a normal position of ledges 22. Inside portions 36 act as a front set of fixed clamp members which are fixed to side portions 14. Positioned outside channel 18 on a front side of holder 10, is a control member set consisting of two control members in the form of buttons 40 each of which is positioned and movable within an opening 15 in a front surface 16 of a corresponding side portion 14. Each control member is connected to channel 18 (including ledges 22) such that moving the control members rearward (into the page, as viewed in FIG. 4) causes the channel 18 to also move rearward, thereby moving ledges 18 (portions of which, beneath inside portions 36 of tabs 30, act as the rear clamp member set) away from portions 36 of tabs 30 (which act as the fixed front clamp member set) to an open position. That is, pressing down on buttons 40 (as viewed in FIG. 4) moves the clamp member sets to an open position. Four springs 72 (seen in FIG. 9) resiliently urge the channel 18 and hence ledges 22 forward toward one another (thereby urging the rear clamp member, composed of portions of ledges 22, to the normal position).

Two spaced apart guides 50 extend from a trailing end of the holder body adjacent respective sides of channel 18. Each guide includes a trailing end 50 and a ledge 54 approximately aligned with a corresponding ledge 22 when the set of ledges 22 (rear clamp member set) is in the open position.

The holder 10 body may carry a machine readable holder identifier 45 which includes data on a characteristic of the holder or seated array unit (such as a holder or array unit dimension or position) or may be linkable to a file containing such data in a similar manner as array unit identifier 115 is linkable to a file, as described above. Such data may be in absolute (for example, a holder or substrate thickness or other dimension) or relative terms (for example, dimension ratios or a distance between an end 12a or side edge 14a and a substrate 110 of an array unit 108 seated in the holder). Such data may include spatial characteristics of the holder 10, substrate 110 of seated array unit 108, or array 112 of seated array unit 108, for example data for any one or more of the foregoing on: x, y and z positions or dimensions; and angular orientation. Other characteristics may include an indication that the holder is or is not suitable for use with: a scanner of specified model or type; an array unit of specified model or type; or a scanner and array unit combination of specified model or types. Such characteristics, particularly when contained in a linked file, may be in the form of a look-up table or other database.

Figure 8:
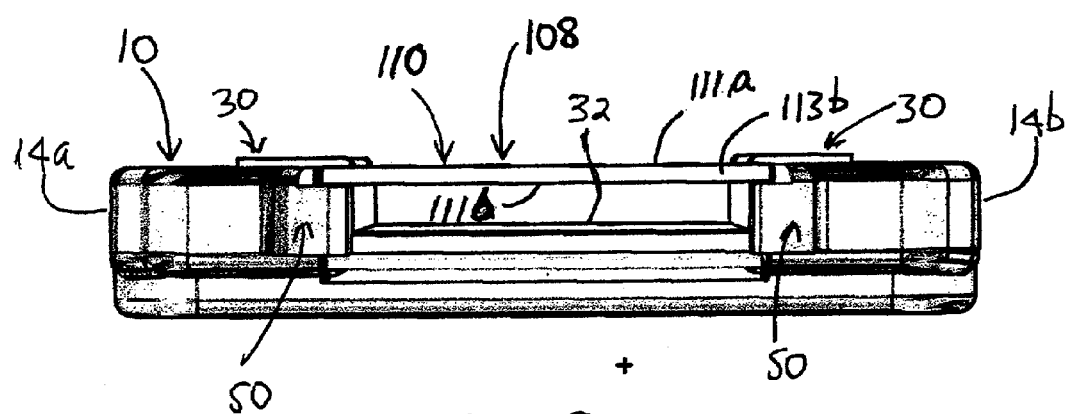
FIG. 8 is a leading end elevation of the holder with mounted slide.

The holder 10 as described, is used to seat slide 110 in a manner as will now be described. First, the array 112 will have typically been previously exposed to a fluid sample and the array 112 washed and dried as described below. At this point a user will typically grip opposing portions of the front and rear surfaces of slide 110 toward the trailing end 113b using their thumb and forefinger. Buttons 40 can then be pressed rearward (into the page as viewed in FIG. 4) to move channel 18 and attached ledges 22 rearward thereby moving the clamp member sets to the open position. Note that when in the open position, the distance between the ledges 22 (movable rear clamp member set) and portions 36 (fixed front clamp member set) is greater than the thickness of slide 110. Leading edge 113a of slide 110 can then be positioned between guides 50 with opposite edges of slide 110 resting on ledges 54 of guides 50, with rear surface 111b (and hence array 112) facing rearward) and bar code 115 facing forward. Slide 110 can then be slid using the gripped portions in an endways direction 120 (see FIG. 6) along ledges 54 of guides 50 and then along ledges 22 of channel 18, between the open clamp member sets, until leading edge 113a of slide 110 abuts leading edge 26 of channel 18 at which point slide 110 is in the seated position (as shown in FIGS. 7 and 8).

Slide 110 is retained in the seated position by releasing buttons 40. Springs 72 then urge ledges 22 (rear clamp member sets) against portions 36 (front clamp member sets), the urging of the clamp member sets against side edge portions of slide 110 causing the slide 110 to be retained in the seated position. Springs 72, ledges 22 and portions 36 then, act as a retaining mechanism on the body of the holder, which mechanism releasably retains an array unit 108 in a seated position within the holder, such that an array unit 108 can be repeatedly inserted into and removed from the seated position in which it is retained in the holder. Since the rear movable clamp member set urges slide 110 against the fixed front clamp member set, this helps ensure that array 112 is in a known fixed position relative to the holder for reading of the array. Note that when in the seated position, rear surface 111b (and hence array 112) is spaced apart from bottom surface 32 (which acts as the backer member). Note also that when slide 110 is in the seated position, the clamp members, and any other portion of the holder, do not contact array 112 or a portion of front surface 111*a* which is opposite array 112. Also, when the slide 110 is in the seated position, trailing end 113*b* is positioned between guides 50. This helps protect trailing end 113*b* from breakage. Furthermore, the gripped position will be between guides 50. The fact that guides 50 extend away from the remainder of the holder such that there are no surfaces or members between guides 50, allows a user to continue to maintain a hold on the gripped portions of the slide 110 until it is in the seated position at which point the gripped portions will also be between guides 50. The array 112 of the seated slide is spaced apart from surface 32 (backer member). This allows backer member 32 to protect array 112 of the seated slide, while the spacing between backer member 32 and array 112 maintains backer member out of the plane of focus of a reader (which will focus on the plane in which array 112 lies on the rear surface 111*b*). This reduces the detection of any fluorescence which might occur from the backer member in response to an interrogating light.

Figure 10:
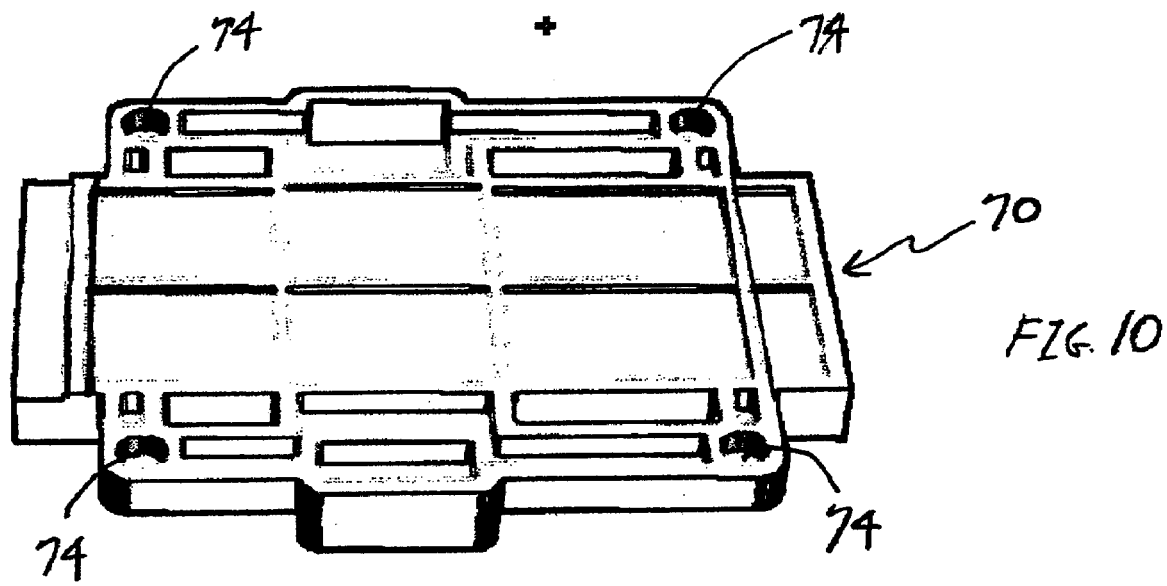
FIGS. 10 and 11 are more detailed views of some of the components shown in FIG. 8.
Figure 11:
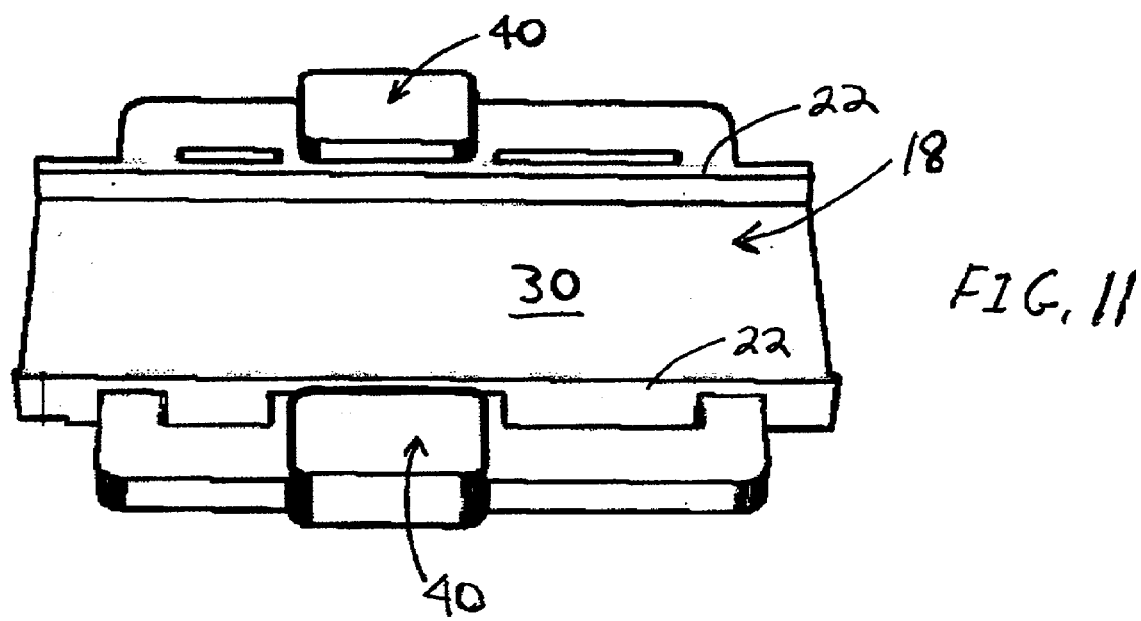

The holder 10 is preferably made in three molded sections from an opaque plastic, such as black ABS plastic (although other materials could be used), as illustrated. In this manner a channel section 70 is interposed between a front section 60 and rear section 80. Rear and front views of channel section 70 are illustrated in more detail in FIGS. 9 and 10, respectively. Channel section is mounted to be free floating between sections 60, 80, with buttons 40 retained and movable forwardly and rearwardly within openings 15. The four springs 72 are retained in openings 74 in a rear side of channel section 70, as best seen in FIG. 10. For ease of manufacturing, sections 60 and 80 of the holder 10 are preferably ultrasonically welded together. Alternatives include adhesive bonding, solvent welding, molded-in snap fit joints and the use of fasteners such as screws. Springs 72 resiliently urge channel section 70 forward, and hence urge buttons 40 and channel 18 forward into the normal position. There is enough spring force behind to ensure that the slide will not move when loads of up to 30 times the force of gravity are applied to the channel in the rearward direction. The color of holder 10 is preferably black to minimize any fluorescent noise or signal contribution from holder 10. Also, holder 10 being opaque prevents any interrogating light from being scattered around inside the scanner. In this context, by the holder being "opaque" is referenced that it typically transmits less than 40%, and preferably less than 10% or 5%, and more preferably less than 2%, of an interrogating light.

Holder 10 may have a maximum length and width each one or both no greater than 100 cm 50 cm, 20 cm or 10 cm, and a thickness no greater than 20 cm, 10 cm or 5 cm.

Figure 12:
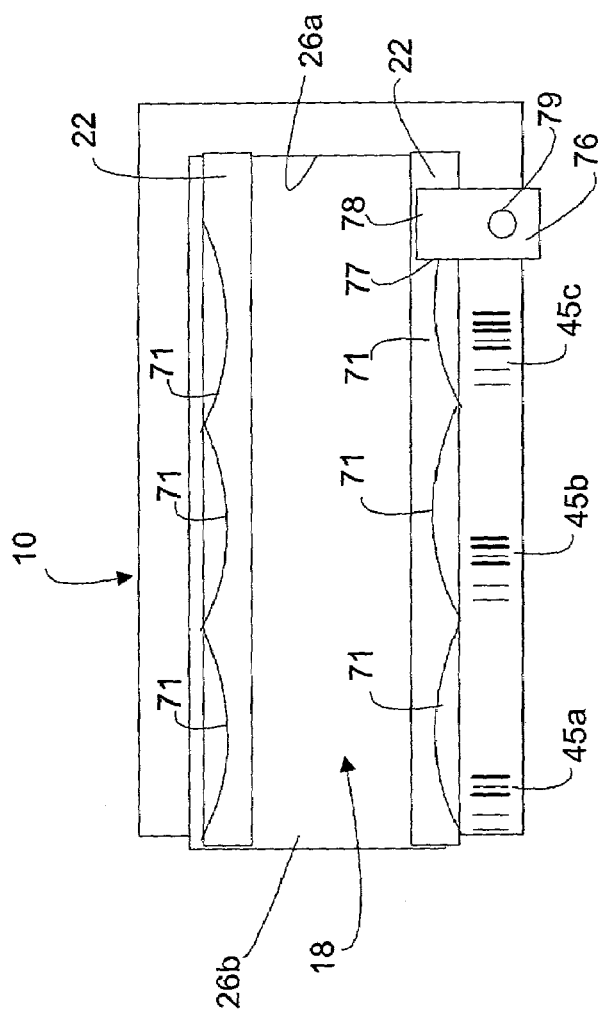
FIG. 12 is a top plan view of another embodiment of a holder of the present invention.

FIG. 12 is a view from above of an alternate embodiment of a holder 10 of the present invention. This embodiment is designed to seat and retain array units having substrates of any one of three different lengths. In this embodiment six springs 71 are provided immediately above ledges 22 to resiliently press against opposed sides 113*c*, 113*d* of an array unit seated therein. In this embodiment then, ledges 22 and springs 71 act as the retaining mechanism which releasably retains an array unit in a seated position, such that an array unit can be repeatedly inserted into and removed from the seated position in which it is retained in the holder. It will be appreciated though, that many other constructions of holder 10, including the retaining mechanism, are possible where the holder releasably retains array units of one or more configurations (for example, various array unit shapes other than rectangular, thicknesses, dimensions, and the like). In the embodiment of FIG. 12 three different identifiers 45*a*, 45*b*, 45*c* in the form of three different bar codes are provided. A clamp 76 is retained on one side of holder 10 and can slide along that side, and has a downwardly extending inside end 78, such that upon tightening of a thumbscrew 79 of clamp 76, clamp 76 will be held in position with the inside end 78 pressing downwardly (into the paper as viewed in FIG. 12) onto the array unit to assist in retaining it in the seated position. If during use of the holder 10 of FIG. 12 a user aligns a side edge 77 of clamp 76 with a leftmost end (as viewed in FIG. 12) of the seated array substrate (of any one of the three lengths), clamp 76 will cover up a corresponding one of identifiers 45*a*, 45*b*, or 45*c*. The length of the seated array unit can then be determined based on which of the identifiers 45*a*, 45*b*, 45*c* can still be read. Thus, in this embodiment the identifiers provide information on an additional characteristic of the seated array unit, namely a dimension (in this case, length) of the seated and retained array unit from among those array units of different dimensions (in this case, lengths) which can be seated and retained in the holder.

Figure 13:
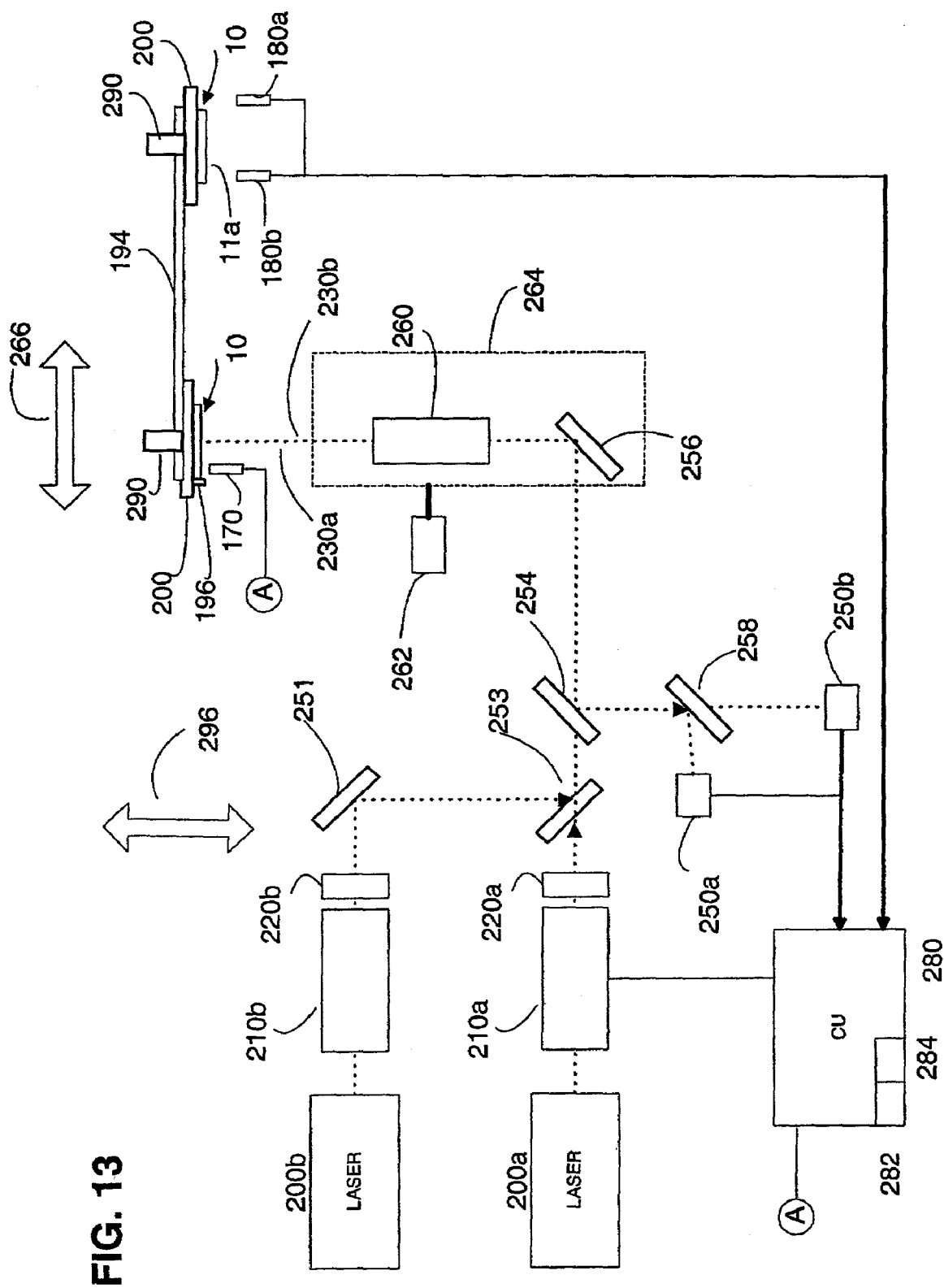
FIG. 13 illustrates an apparatus of the present invention.
Figure 14:
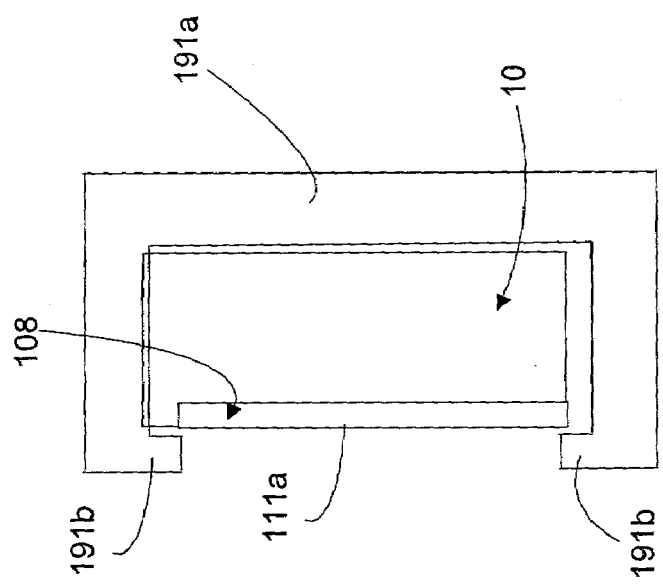
FIG. 14 is an end view of a holder receptacle in the apparatus of FIG. 13.
Figure 15:
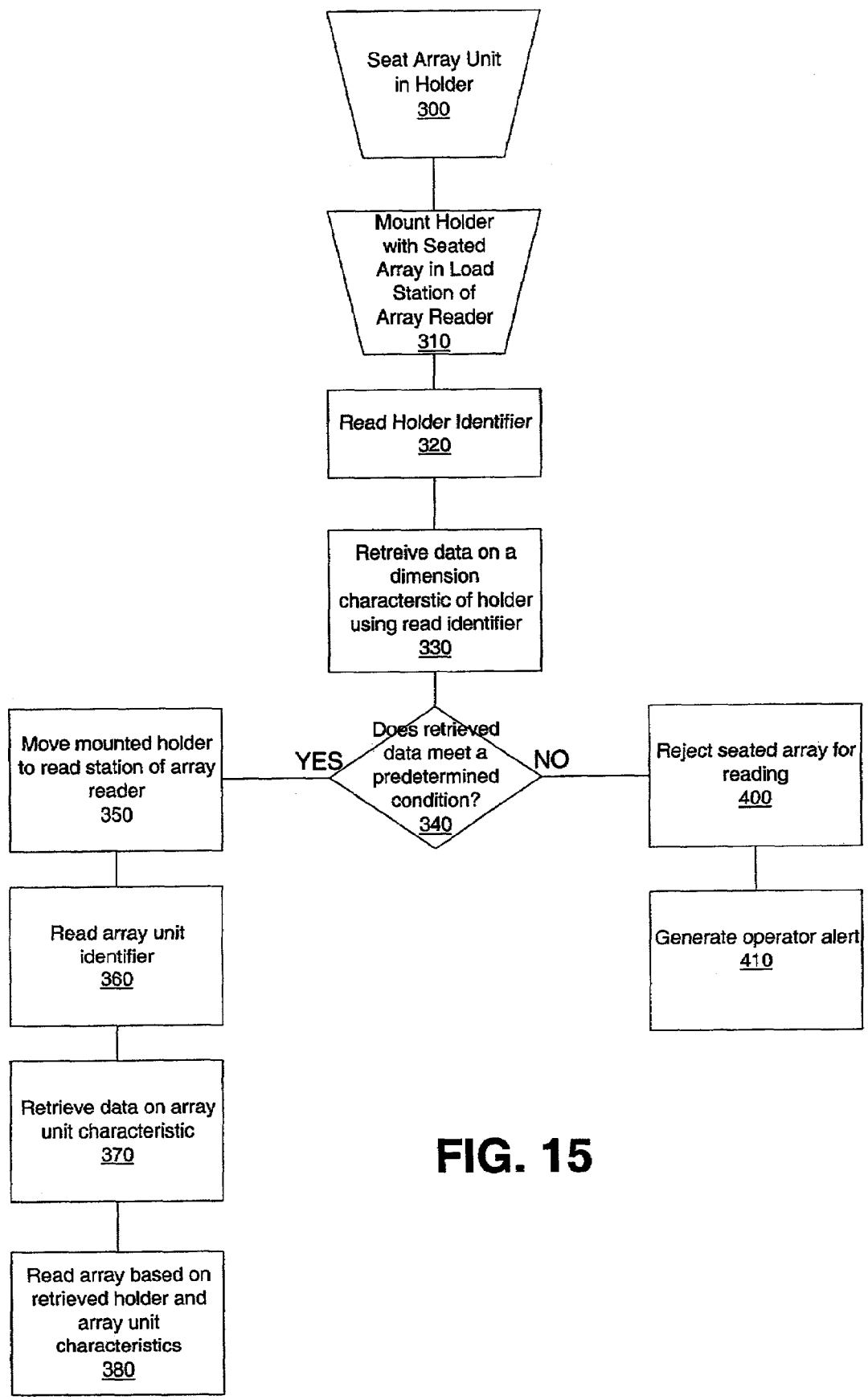
FIG. 15 is a flow chart showing a method of the present invention.

Referring now to FIG. 13, an apparatus of the present invention (which may be generally referenced as an array reader in the form of an array scanner) is illustrated. The scanner shown has a holder 10 mounted in a receptacle 200 of the scanner, which mounted holder 10 has a seated array unit 108 (which may be referenced as a "received array unit 108", and the array thereof referenced as a "received array 112"). Receptacle 200 and the transporter 290 which moves it are shown positioned at a read station in the left hand depiction of receptacle 200 in FIG. 13 (in line with paths 230*a*, 230*b*), and at a load station in right hand side depiction in FIG. 13 (in line with readers 180*a*, 180*b*). Receptacle 200 moves between the load station and read station positions along tracks 194 by transporter 290 (which is under control of a control unit 280). In practice, the actual direction of tracks 194 in FIG. 13 and the movement of receptacle 200 between the load and read stations may be in a direction in and out of the paper as viewed in FIG. 13. Receptacle 200 is of a slotted configuration as best seen in the end view of FIG. 14 with a channel member 191*a* and two inward extensions 191*b* retaining a holder 10 in a mounted position, as seen in FIG. 14. One end (a leftmost end in FIG. 13) is closed by a stop 196 while the other end (the rightmost end as viewed in FIG. 13) is open.

A holder 10 may be mounted in receptacle 200 by sliding into the open end, or de-mounted therefrom by a reverse procedure, using an automated loader arm (not shown) under control of control unit 280. This may be performed manually by an operator or automatically by control unit 280 from a linear tray or a circular carousel carrying many holders, with each holder moving into alignment with receptacle 200 in turn. Also positioned at the load station are first reader 180*a* to read holder identifier 45 and a second reader 180*b* which reads an array unit identifier 115. When those identifiers 45, 115 are in the form of bar codes, each of those readers may be a suitable bar code reader. While readers 180*a*, 180*b* are shown positioned at the load station, other positioning will be appreciated. For example, reader 180*b* could be positioned in the reader station. Similarly, either or both of the readers 180*a*, 180*b* could be positioned at the load station (or elsewhere, even outside of the scanner for manual use by an operator) to read the respective identifiers of a holder before it is mounted in receptacle 200. Identifier readers 180*a*, 180*b* together with the array reader components described above, form components of a reader system to read the holder identifier, array unit identifier, and data from different chemical moieties of the array.

A light system provides light from a laser 200 which passes through an electro-optic modulator (EOM) 210 with attached polarizer 220. Each laser 200a, 200b may be of different wavelength (for example, one providing red light and the other green) and each has its own corresponding EOM 210a, 210b and polarizer 220a, 220b. The resulting interrogating light beams are coherent and monochromatic, and are directed along respective paths 230a, 230b toward front surface 11a of received array 112, by the use of full mirror 251 and dichroic mirror 253. While FIG. 13 shows these paths as being coincident for the sake of simplicity, the two may in fact be separated by an angle so as to an array at different locations. This angle of separation may be such that each interrogating light beam is directed along path 230a, 230b toward back surface 11b at an angle equal to or greater than 0 degrees, and up to 45 degrees to a normal to the back surface (for example less than 5, or 1 degrees, such as 0.5 degrees). Such an arrangement allows the two interrogating light beams to pass through the same optical system while reducing saturation of fluorescent labels at features 116 as well as channel cross-talk. A control signal in the form of a variable voltage applied to each corresponding EOM 210a, 210b by the controller (CU) 280, changes the polarization of the exiting light which is thus more or less attenuated by the corresponding polarizer 220a, 220b. Controller 280 may be or include a suitably programmed processor. Thus, each EOM 210 and corresponding polarizer 220 together act as a variable optical attenuator which can alter the power of an interrogating light spot exiting from the attenuator. The remainder of the light from both lasers 200a, 200b is transmitted through a dichroic beam splitter 254, reflected off fully reflecting mirror 256 and focused through substrate onto received array 112, using optical components in beam focuser 260. Light emitted, in particular fluorescence, at two different wavelengths (for example, green and red light) from features 116, in response to the interrogating light, is imaged using the same optics in focuser/scanner 260, and is reflected off mirrors 256 and 254. The two different wavelengths are separated by a further dichroic mirror 258 and are passed to respective detectors 250a and 250b. More optical components (not shown) may be used between the dichroic and each detector 250a, 250b (such as lenses, pinholes, filters, fibers etc.) and each detector 250a, 250b may be of various different types (e.g. a photomultiplier tube (PMT) or a CCD or an avalanche photodiode (APD)). All of the optical components through which light emitted from an array 112 in response to the illuminating laser light, passes to detectors 250a, 250b, together with those detectors, form a detection system. This detection system has a fixed focal plane.

A scan system under control of control unit 280 causes the illuminating area in the form of a light spot from each laser 200a, 200b, and a detecting area of each detector 250a, 250b (which detecting area will form a pixel in the detected image), to be scanned across multiple regions of the received array 112. In this manner, each of the multiple features 16 of the array is read, with each read feature containing multiple pixels (for example, more than five, ten, or twenty). In particular the scanning system is typically a line by line scanner, scanning the interrogating light spot in a line across a received array 112, in a direction of arrow 266, then moving ("transitioning") the interrogating light in a direction into/out of the paper as viewed in FIG. 5 to a position at an end of a next line, and repeating the line scanning and transitioning until the entire array 112 has been scanned. This can be accomplished by providing a housing 264 containing mirror 258 and focuser 260, which housing 264 can be moved along a line of pixels (that is, from left to right or the reverse as viewed in FIG. 13) by a transporter 262. The second direction scanning (line transitioning, which is in and out of the paper as viewed in FIG. 5) can be provided by second transporter which may include a motor and belt (not shown) to move holder 200 along one or more tracks. The second transporter may use a same or different actuator components to accomplish coarse (a larger number of lines) movement and finer movement (a smaller number of lines). Note that each pixel on the array which can be illuminated and from which any resulting emitted light can be simultaneously (or shortly thereafter) detected, are typically substantially smaller than an array feature 116 (typically having an area about $\frac{1}{10}$ to $\frac{1}{100}$ the area of a feature).

An autofocus offset detector 170 is also provided to sense any offset between different locations on a received array 112 in the reading station, and a determined position of the focal plane of the detection system. An autofocus system includes detector 170, control unit 280, and a motorized adjuster to move holder in the direction of arrow 196. A suitable chemical array autofocus system is described in pending U.S. patent application Ser. No. 09/415,184 for "Apparatus And Method For Autofocus" by Dorsel et al., filed Oct. 7, 1999, incorporated herein by reference, as well as European publication EP 1091229 published Apr. 11, 2001 under the same title and inventors.

Controller 280 of the apparatus is connected to receive signals from detectors 250a, 250b (these different signals being different "channels"), namely a signal which results at each of the multiple detected wavelengths from emitted light for each scanned pixel on a received array 112 when at the reading position mounted in holder 200. Controller 280 also receives the signal from autofocus offset detector 170, and provides the control signal to EOM 210, and controls the scan system. Controller 280 may also analyze, store, and/or output data relating to emitted signals received from detectors 250a, 250b in a known manner. Controller 280 may include a computer in the form of a programmable digital processor, and include the following: a memory 282 which can be a solid state, optical, or magnetic memory device such as a drive to read a portable removable media (such as a magnetic or optical disk); and a communication module 284 which can communicate over a communication channel (such as a network, for example the internet or a telephone network) with a remote site (such as a database at which information relating to holder 10 or an array unit 108 may be stored in association with the holder identifier 45 and array identifier 115, respectively). Controller 280 is suitably programmed to execute all of the steps required by it during operation of the apparatus, as discussed further below. Alternatively, controller 280 may be any hardware or hardware/software combination which can execute those steps.

All of the components of the scanner shown in FIG. 13 may be located in a same housing which may have any one or more of its three dimensions larger than 10 cm, 20 cm, or 100 cm, and smaller than 500 cm, 300 cm, 200 cm, or 100 cm.

In one mode of operation, the features 116 of array 112 on an array unit 108 are simultaneously exposed to a sample such as by contacting the different features 116 simultaneously with a layer of the same sample fluid, such that at least some of the features bind to respective moieties in the sample which sample moieties include the fluorescent label. For example, different polynucleotide sequences at respective features 116 can each hybridize to a fluorescently labeled complementary sequence from the sample. The array may then be washed with buffer then water, and dried following washing then inserted into a scanner for reading. Drying may be accomplished using any suitable drying method and conditions which will not decompose the probes and their bound targets, such as any suitable one or more of: air drying at room temperature or raised temperature; reduced pressure; centrifuging; or exposure to a dry unreactive gas stream (such as dry nitrogen).

The array 112 is then ready for reading. The sequence of events which next occur can be understood with particular reference to FIGS. 13 and 14 (reference numbers in parentheses represent processes shown in FIG. 14). First, the array unit 108 is manually seated (300) in holder 10 by being slid into end 26*b* as described above, and the resulting holder 10 with seated array 108 then manually mounted (310) in receptacle 200 while at the load station of the array reader of FIG. 13, or automatically mounted therein from a carousel or tray as previously described. Any or all of the remainder of the following steps can then be executed automatically by control unit 280 or can await operator command through a user interface (not shown). The holder identifier 45 is then read (320) by first reader 180*a*. If second reader 180*b* is in the location shown in FIG. 13 then at this time it can read (360) array unit identifier. However, if second reader 180*b* is at the read station as mentioned above, then this can be done later. Data is then retrieved (330) for a characteristic of mounted holder 10. As mentioned before, this data may simply be data on the suitability of use of holder 10 in the particular scanner of FIG. 13, or alternatively or additionally it may include a spatial characteristic of the holder (such as x, y, and z dimensions) as well as data on the position of the seated array unit 108 (for example, the position of substrate 110 in relation to some component of holder 10 such as any of the edges or a back surface). This retrieved data can then be checked (340) to see if it meets a predetermined condition. By predetermined condition in this context is any condition which control unit 280 has access to, such as one stored in memory 282. Such predetermined conditions can include maximum limits on any one or more of a an x, y, and z dimension of a holder 10 which the scanner can handle, or an identification of serial numbers, manufacturers or other designations for holders which are or are not suitable for use in the scanner.

If the predetermined condition is met, the mounted holder 10 can be moved (350) to the read station of the scanner while remaining mounted in receptacle 200. At this point the array unit identifier 115 can be read (360) if it has not already been read, as previously discussed. Data on array unit characteristics can then be retrieved (370) based on the read array unit identifier. Such data can include, for example, any one or more of array layout, and x, y, and z positions or dimensions of received array 112. The received array 112 can then be read based on the retrieved array 112 and holder 10 characteristics. For example, the retrieved x and y position of array 112 together with the retrieved data on the position of the seated array unit in holder 10, can be used to precisely define in space the region over which the laser beams are scanned. Also, the retrieved z position data for a location of a seated array in holder 10, along with retrieved z position data for array 112 on substrate 110 (for example, such data may be the thickness of substrate 110) can be used as a basis for adjusting the position of the focal plane of the detection system relative to a received array 112 such that the focal plane coincides with the plane in space at which the received array 112 is located.

If the predetermined condition (or any one of multiple predetermined conditions) is not met (for example, holder 10 is unsuitable for use in a scanner of FIG. 13 or has dimensions which are too large), the seated array 112 in holder 10 is rejected (400) for reading. The rejection can be accomplished simply by control unit 280 doing any one or more of: not moving holder 10 into the read station; turning off the power to the remainder of the scanner; and generating an audible or visual operator alert 410 on a speaker of monitor (not shown).

As mentioned previously, data based on holder identifier 45 or array unit identifier 115 can be retrieved by retrieving them directly from the read identifier (where the data is contained in them). Alternatively, either identifier may be used to retrieve some or all of the data from a database containing the identifier in association with such data. Such a database may be a local database accessible by controller 280 (such as may be contained in a portable storage medium in drive 282 which is associated with a package carrying a holder 10 or array unit 110, such as by physical association by being in the package when received by the user, or by a suitable identification), or may be a remote database accessible by controller 280 through communication module 284 and a suitable communication channel (not shown).

The saved results from a sample exposed array, read according to a method of the present invention, may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample). The results of the reading (processed or not) may be forwarded (such as by communication of data representing the results) to a remote location if desired, and received there for further use (such as further processing). Transporter 290 can then move receptacle 200 and mounted holder 10 back to the load station where it can be demounted by the procedure the reverse of the mounting procedure, and another holder 10 with seated array 110 mounted in holder 200, and the entire cycle repeated as often as desired.

Various modifications to the above embodiments can be made. For example, a variety of geometries of the features 116 may be constructed other than the organized rows and columns of the array 112 of FIGS. 1–3. For example, features 116 can be arranged in a series of curvilinear rows across the substrate surface (for example, a series of concentric circles or semi-circles of spots), and the like. Even irregular arrangements of features 116 can be used, at least when some means is provided such that during their use the locations of features of particular characteristics can be determined (for example, a map of the features is provided to the end user in a package with the array or is retrieved based on the array identifier 115). Furthermore, substrate 110 could carry more than one array 112, arranged in any desired configuration on substrate 110. While substrate 10 is planar and rectangular in form, other shapes (for example, circular) could be used with holder 10 being adjusted accordingly. It will be appreciated that both flexible and rigid substrates may be used, provided such a suitable holder is used. Substrate materials provide physical support for the deposited material and endure the conditions of the deposition process and of any subsequent treatment or handling or processing that may be encountered in the use of the particular array. Additionally, during scanning it is possible to illuminate all pixels of a line simultaneously (for example, by using a line of light emitting diodes).

While the invention has been described in relation to an array reader in the form of a fluorescence scanner, the holders and methods of the present invention can be used in connection with readers other than fluorescence scanners. For example, other reading methods include other optical techniques (for example, detecting chemiluminescent or electroluminescent labels) or electrical techniques (where each feature is provided with an electrode to detect hybridization at that feature in a manner disclosed in U.S. Pat. Nos. 6,251,685, 6,221,583 and elsewhere). In optical reading techniques the holder or seated array unit characteristics may still be used in the reading. For electrical techniques the foregoing characteristics may be used to determine location of electrical connections on a seated array unit or the suitability in a particular reader based, for example, on incompatibility of locations of electrical connections.

The substrate surface onto which the polynucleotide compositions or other moieties is deposited may be smooth or substantially planar, or have irregularities, such as depressions or elevations. The surface may be modified with one or more different layers of compounds that serve to modify the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers of interest include: inorganic and organic layers such as metals, metal oxides, polymers, small organic molecules and the like. Polymeric layers of interest include layers of: peptides, proteins, polynucleic acids or mimetics thereof (for example, peptide nucleic acids and the like); polysaccharides, phospholipids, polyurethanes, polyesters, polycarbonates, polyureas, polyamides, polyethyleneamines, polyarylene sulfides, polysiloxanes, polyimides, polyacetates, and the like, where the polymers may be hetero- or homopolymeric, and may or may not have separate functional moieties attached thereto (for example, conjugated).

Various further modifications to the particular embodiments described above are, of course, possible. Accordingly, the present invention is not limited to the particular embodiments described in detail above.

What is claimed is:

1. A holder for an array unit having a planar substrate and an array of chemical moieties on a surface of the substrate, the holder comprising:
    a body with a retaining mechanism which releasably retains an array unit in a seated position, such that an array unit can be repeatedly inserted into and removed from the seated position in which it is retained in the holder, wherein the retaining mechanism comprises rear clamp member sets comprising ledges and front clamp member sets wherein the sets urge against side edge portions of a seated array unit causing the array unit to be retained in a seated position; and
    a machine readable holder identifier which includes data on a characteristic of the seated array.

2. A holder according to claim 1 further comprising springs that urge the rear clamp member sets and the front clamp member sets.

3. A holder according to claim 1 wherein the machine readable holder identifier includes data selected from the group consisting of suitability of use of the holder in an array scanner, dimensions of the holder, dimensions of a seated array unit in the holder, data on the position of a seated array unit in the holder and combinations thereof.

4. A holder according to claim 1 wherein the holder identifier includes data on the position or dimension of the substrate of an array unit seated in the holder unit wherein the position or dimension data includes data on the x, y, or z positions or dimensions of the substrate of the seated array unit, where x and y are the directions along the length and width of the substrate and z is the direction perpendicular to the substrate plane.

5. A holder according to claim 1 wherein the position or dimension data includes data on the z position of the substrate of the seated array unit.

6. A holder according to claim 1 wherein the position data includes data on the angular orientation of the substrate of the seated array unit.

7. A holder according to claim 1 wherein the holder identifier comprises a bar code or is carried in a memory attached to the remainder of the holder.

8. A holder according to claim 1 wherein the holder additionally comprises a magnetic or solid state memory attached to the body and the identifier is carried by the memory.

9. A holder according to claim 1 additionally comprising a seated array unit.

10. A holder according to claim 9 wherein the seated array unit additionally includes an array unit identifier.

11. A holder according to claim 10 wherein the array unit identifier is a machine readable identifier.

12. A holder according to claim 11 wherein the array unit identifier comprises a bar code or is carried in a memory attached to the remainder of the array unit.

13. A holder according to claim 9 wherein the machine readable holder identifier is a bar code and the seated array comprises an array identifier that is a bar code.

14. A holder according to claim 1 which has a maximum length and width each no greater than 50 cm, and a thickness no greater than 10 cm.

15. A holder for an array unit having a planar substrate and an array of chemical moieties on a surface of the substrate, the holder comprising:
    a body with a retaining mechanism which releasably retains an array unit in a seated position, such that an array unit can be repeatedly inserted into and removed from the seated position in which it is retained in the holder, wherein the retaining mechanism comprises rear clamp member sets comprising ledges and front clamp member sets wherein the sets urge against side edge portions of a seated array unit causing the array unit to be retained in a seated position;
    springs that urge the rear clamp member sets and the front clamp member sets; and
    a machine readable holder identifier which includes data on a characteristic of the seated array.

16. A holder according to claim 15 wherein the machine readable holder identifier includes data selected from the group consisting of suitability of use of the holder in an array scanner, dimensions of the holder, dimensions of a seated array unit in the holder, data on the position of a seated array unit in the holder and combinations thereof.

* * * * *